US00PP16583P2

(12) United States Plant Patent
Olesen

(10) Patent No.: US PP16,583 P2
(45) Date of Patent: May 30, 2006

(54) SHRUB ROSE PLANT NAMED 'POULTC006'

(50) Latin Name: *Rosa hybrida*
Varietal Denomination: Poultc006

(75) Inventor: Mogens Olesen, Fredensborg (DK)

(73) Assignee: Poulsen Roser A/S, Fredensborg ( * ) Notice: Subject to any disclaimer, the term of this patent is extended or adjusted under 35 U.S.C. 154(b) by 121 days.

(21) Appl. No.: 11/002,352

(22) Filed: Dec. 1, 2004

(51) Int. Cl.
*A01H 5/00* (2006.01)

(52) U.S. Cl. ..... Plt./108

(58) Field of Classification Search ..... Plt./108, Plt./150

See application file for complete search history.

*Primary Examiner*—Anne Marie Grunberg
*Assistant Examiner*—June Hwu

(57) ABSTRACT

A new garden rose plant of the shrub rose class which has abundant, red flowers and attractive foliage. This new and distinct variety has shown to be uniform and stable in the resulting generations from asexual propagation.

3 Drawing Sheets

Botanical classification: *Rosa hybrida.*
Variety denomination: 'Poultc006'.

SUMMARY OF THE INVENTION

The present invention constitutes a new and distinct variety of garden rose plant which originated from a controlled crossing between the female seed parent, a variety by the same inventors named 'Poulharmu', described and illustrated in U.S. Plant Pat. No. 12,681 dated Jun. 11, 2002, and the male pollen parent, an unnamed seedling. The two parents were crossed during the summer of 1997, and the resulting seeds were planted in a controlled environment in Fredensborg, Denmark. The new variety is named 'Poultc006'.

The new variety may be distinguished from its female seed parent by the following combination of characteristics:

1. 'Poulharmu' has a general tonality of flower color Red Group 44B, while 'Poultc006' is Red Group 50A to Red Group 46C.
2. 'Poultc006' has more flower petals than 'Poulharmu'.

The new variety may be distinguished from the male pollen parent plant by the following combination 1. The pollen parent has smaller leaves and leaflets than 'Poultc006'.
2. The pollen parent has a general tonality of flower color of Red Group 43B while 'Poultc006' is Red Group 50A to Red Group 46C.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Disease resistance.

This combination of qualities is not present in previously available commercial cultivars of this type, known to the inventor, and distinguish 'Poultc006' from all other varieties of which we are aware.

As part of the rose development program, Mogens N. Olesen germinated the seeds from the aforementioned hybridization during winter of 1998 and conducted evaluations on the resulting seedlings in a controlled environment in Fredensborg, Denmark.

'Poultc006' was selected in the spring of 1998 by the inventor as a single plant from the progeny of the aforementioned hybridization.

Asexual reproduction of 'Poultc006' by traditional budding and rooted cuttings was first done by Mogens N. Olesen in the nursery in Fredensborg, Denmark in July 1998.

This initial and other subsequent asexual propagations conducted in controlled environments have demonstrated that the characteristics of 'Poultc006' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poultc006'. Specifically illustrated in the drawings are:

FIG. 2.1; Flower buds attached to peduncle;

FIG. 2.2; Open flower, above view and sepals, pedicel, and receptacle;

FIG. 2.3; Partially opened flowers, side view.

FIG. 2.4; Flower petals, detached;

FIG. 2.5; Bare stem exhibiting thorns;

FIG. 2.6; Mature leaves;

FIG. 3.1 Juvenile leaves;

FIG. 3.2 Mature leaves attached to stem;

FIG. 3.3 Mature leaves.

DETAILED DESCRIPTION OF THE VARIETY

Figure 1:
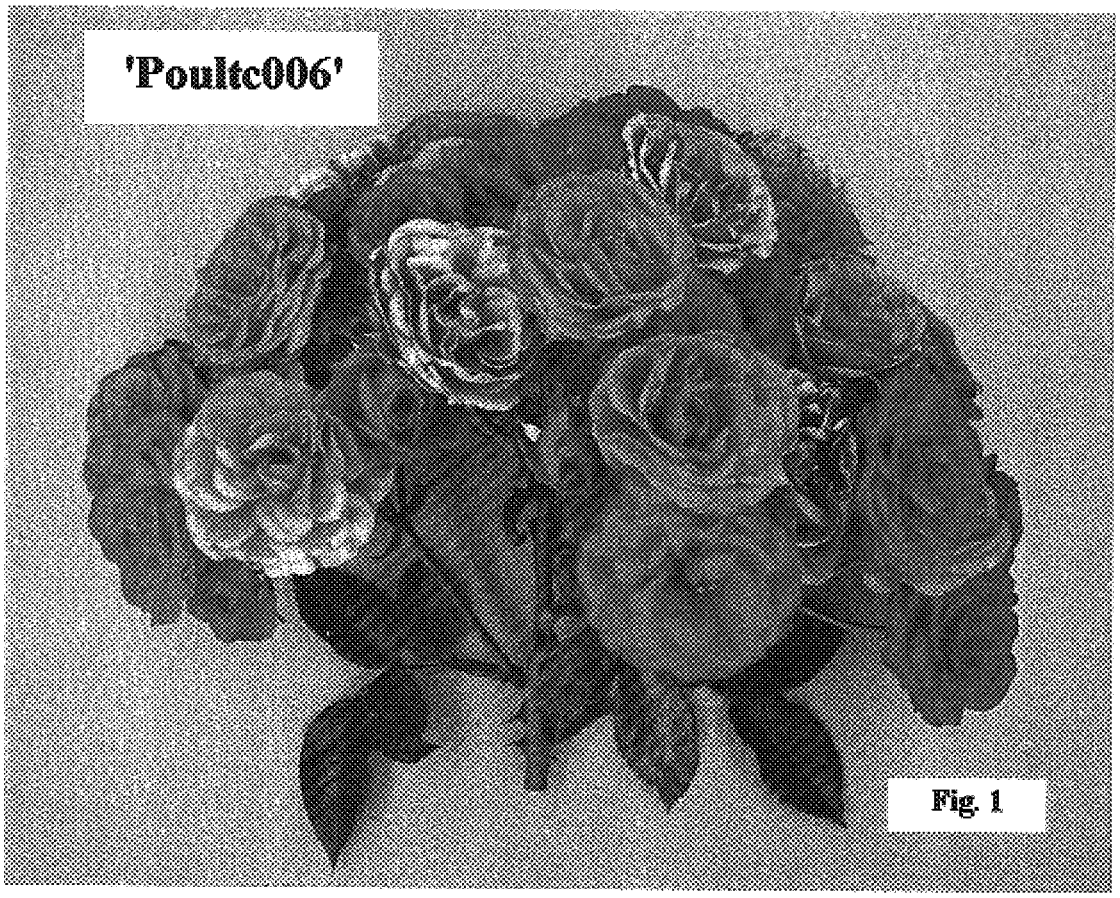
FIG. 1.1; Cluster of open flowers.

The following is a description of 'Poultc006', as observed in its growth in a field nursery in Jackson County, Oreg. Observed plants are 3 years of age, and were grown on *Rosa*

*multiflora* understock. Color references are made using The Royal Horticultural Society (London, England) Colour Chart, 1995, except where common terms of color are used.

For a comparison, several physical characteristics of the rose variety 'Poultw002', a rose variety from the same inventors described and illustrated in U.S. Plant Pat. No. 15,230 dated Oct. 12, 2004, are compared to 'Poultc006' in Chart 1.

CHART 1

| | 'Poultc006' | 'Poultw002' |
|---|---|---|
| Number of thorns per 10 cm of stem | 11 | 32 |
| General Tonality | Red Group 50A to Red Group 46C | Red-Purple Group 57A to 57B |
| Petalage | 35 petals | 25 to 30 petals. |

FLOWER AND FLOWER BUD

Blooming habit: Continuous.

Flower bud:

*Size.*—Upon opening, 17 mm in length from base of receptacle to end of bud. Bud diameter is 10 mm.

*Bud form.*—Urceolate.

*Bud color.*—As sepals unfold, petals are Red Group 50A to Red-Purple Group 63A.

*Sepal inner surface.*—Color: Greyed-Green Group 191B. Pubescence: Abundant.

*Sepal outer surface.*—Color: Yellow-Green Group 144A and Green Group 138A blend. Strong anthocyanic pigments the color of Greyed-Purple Group 187A observed. Texture: Smooth with few stipitate glands.

*Sepal shape.*—Sepal apex is cirrhose. Base is flat at union with receptacle.

*Sepal margin.*—Margins have medium foliaceous appendages, extending 5 mm, on three of the five sepals.

*Sepal size.*—18 mm (l) by 8 mm (w).

*Receptacle.*—Texture: Smooth. Shape: Urn-shaped. Size: 4 mm (h)×6 mm (w). Color: Yellow-Green Group 144A. Strong anthocyanic pigments the color of Greyed-Purple Group 187B observed.

Pedicel:

*Surface.*—Somewhat rough due to presence of stipitate glands.

*Length.*—35 mm on average.

*Diameter.*—2 mm on average.

*Color.*—Yellow-Green Group 144B. Anthocyanic pigments the color of Greyed-Purple Group 184B observed.

*Strength.*—Weak.

Flower bud development: Flower buds are borne in clusters of 15 to 21 flower buds per stem. Inflorescence type is a panicle.

Flower bloom:

*Fragrance.*—Moderate floral scent.

*Duration.*—The blooms have a duration on the plant of approximately 7 to 10 days. Petals fall cleanly away from plant.

*Size.*—Flower diameter is 46 mm when open. Flower depth is 21 mm.

*Flower shape.*—General shape is an open cup, double flower, with petals that curve out from the center.

*Shape of flower, side view.*—Upon opening, the upper portion of the flower is flattened convex. The lower portion is concave. After flowers have completely opened the upper portion is flattened convex.

Petalage: Under normal conditions, flowers have 35 petals total, 3 to 4 of which are petaloids.

Petal color:

*Upon opening, outer petals.*—Upper surface: Red Group 50A with intonations of Red Group 45B blended occasionally with streaks of White Group 155A observed. Lower surface: Red Group 52A, occasionally with streaks of White Group 155A observed.

*Upon opening, inner petals.*—Upper surface: Red Group 50A with light intonations of Red Group 45A blended in occasionally with streaks of White Group 155A observed. Lower surface: Red Group 52A, occasionally with streaks of White Group 155A observed.

*Basal petal spots, upon opening.*—Upper surface: White Group 155A. Lower surface: White Group 155A.

*After opening, outer petals.*—Upper surface: Red Group 50A with intonations of Red Group 45B blended occasionally with streaks of White Group 155A observed. Lower surface: Red Group 52A, occasionally with streaks of White Group 155A observed.

*After opening, inner petals.*—Upper surface: Red Group 50A with light intonations of Red Group 45A blended in occasionally with streaks of White Group 155A observed. Lower surface: Red Group 52A, occasionally with streaks of White Group 155A observed.

*Basal petal spots, after opening.*—Upper surface: White Group 155A. Lower surface: White Group 155A.

*Guard petals.*—Occasionally 1 or 2 outermost guard petals have distinct coloration. Upper surface: Red Group 50A to Red Group 45B with streaks of Yellow-Green Group 144B. Lightly pubescent. Lower surface: Red Group 52A with streaks of Yellow-Green 144B. Lightly pubescent. Shape: General shape is irregular to broad elliptical. Apex: Mucronate. Base: Acute. Texture: Lightly pubescent.

General tonality: On open flower Red Group 50A to Red Group 46C. No change in the general tonality at the end of the 7th day. Afterwards, general tonality is Red Group 52A.

Petals:

*Petal reflex.*—Slight to none.

*Margin.*—Entire. Weak undulations of margin observed.

*Shape.*—Generally narrow elliptical in shape. Apex: Occasionally emarginate. Base: Acute. Size: 18 mm (l)×18 mm (w).

*Texture.*—Smooth.

*Thickness.*—Somewhat thin.

*Arrangement.*—Not Formal.

Petaloids:

*Size.*—11 mm (l)×7 mm (w).

*Shape.*—Irregular.

*Color.*—Red Group 50A to Red Group 46C.

Reproductive organs:

*Pollen.*—None observed.

*Anthers.*—Size: 2 mm in length. Color: Center is Yellow-White Group 158D with margins Greyed-Orange Group 163B. Quantity: Normally 125.

*Filaments.*—Color: Yellow-Green Group 144D. Length: 4 mm.

*Pistils.*—Length: 5 mm. Quantity: Normally 100.

*Stigmas.*—Level in location relative to the length of the filaments and the height of the anthers. Color: Greyed-Yellow Group 162C.

*Hips.*—None Observed in the field nursery in Jackson County Oreg.

PLANT

Plant growth: Moderate, upright to bushy. When grown as a budded field grown plant on *Rosa multiflora* understock, the average height of the plant is 60 to 100 cm and the average width is 60 cm.

Stems:

*Color.*—Juvenile growth: Yellow-Green Group 144B. Mature growth: Yellow-Green Group 146B to 146C.

*Length.*—On average, canes are 50 to 60 cm from the base of the plant to the flowering portion.

*Diameter.*—10 mm.

*Internodes.*—On mature canes, there is an average distance of 26 mm between nodes.

*Surface texture.*—Young wood: Rough with numerous prickles. Older wood: Rough with numerous prickles.

Thorns:

*Incidence.*—11 thorns per 10 cm of stem.

*Size.*—Average length of thorns on mature stems is 7 mm.

*Shape.*—Concave.

*Color.*—Juvenile thorns are Greyed-Purple Group 184A. Mature thorns are Greyed-Orange Group 174B at the base and Greyed-Orange Group 166A towards the apex.

Plant foliage: 5 to 7 leaflets normally present on leaves at the middle of the stem.

*Compound leaf.*—120 mm in length, 100 mm wide.

*Quantity.*—3 leaves per 10 cm of stem on average.

*Color of mature foliage.*—Upper side: Yellow-Green Group 147A. Lower side: Yellow-Green Group 147B.

*Color of juvenile foliage.*—Upper side: Yellow-Green Group 146C to Green Group 143B. Rachis, petiole and margins are Greyed-Purple Group 183A. Lower side: Yellow-Green Group 146C.

Plant leaves and leaflets:

*Stipules.*—Size: 17 to 20 mm in length. Shape: Linear, slightly broad based with outward extending apecies. Margins: Finely serrated with many stipitate glands. Color: Green Group 143A. Anthocyanin: None.

*Petiole.*—Length: 20 mm. Diameter: 2 mm.

*Upper surface.*—Color: Greyed-Red Group 180C to Greyed-Orange Group 163D.

*Lower surface.*—Color: Yellow-Green Group 145B. Observations: Few stipitate glands and small prickles observed.

*Rachis.*—Length: 60 mm. Upper surface: Color: Yellow-Green Group 146C.

*Lower surface.*—Color: Yellow-Green Group 145C. Observations: Few stipitate glands and small prickles observed.

*Leaflet.*—Edge: Doubly serrated. Size: Average size of the terminal leaflet on normal leaves is 46 mm in length by 26 mm wide. Shape: Generally elliptical. Base: Obtuse. Apex: Acuminate. Texture: Smooth. Thickness: Average. Arrangement: Odd pinnate. Venation: Reticulate. Glossiness: Moderate finish.

Disease resistance: Above average resistance to powdery and downy mildews, rust, black spot, and *Botrytis* under normal growing conditions in Jackson County, Oreg.

Cold hardiness: The variety 'Poultc006' has been found to be cold tolerant to USDA Cold Hardiness Zone 6.

It is claimed:

1. A new and distinct variety of rose plant of the shrub rose class named 'Poultc006' substantially as illustrated and described herein as a distinct and novel rose variety due to its abundant red flowers, disease resistance, and extended period of bloom.

* * * * *

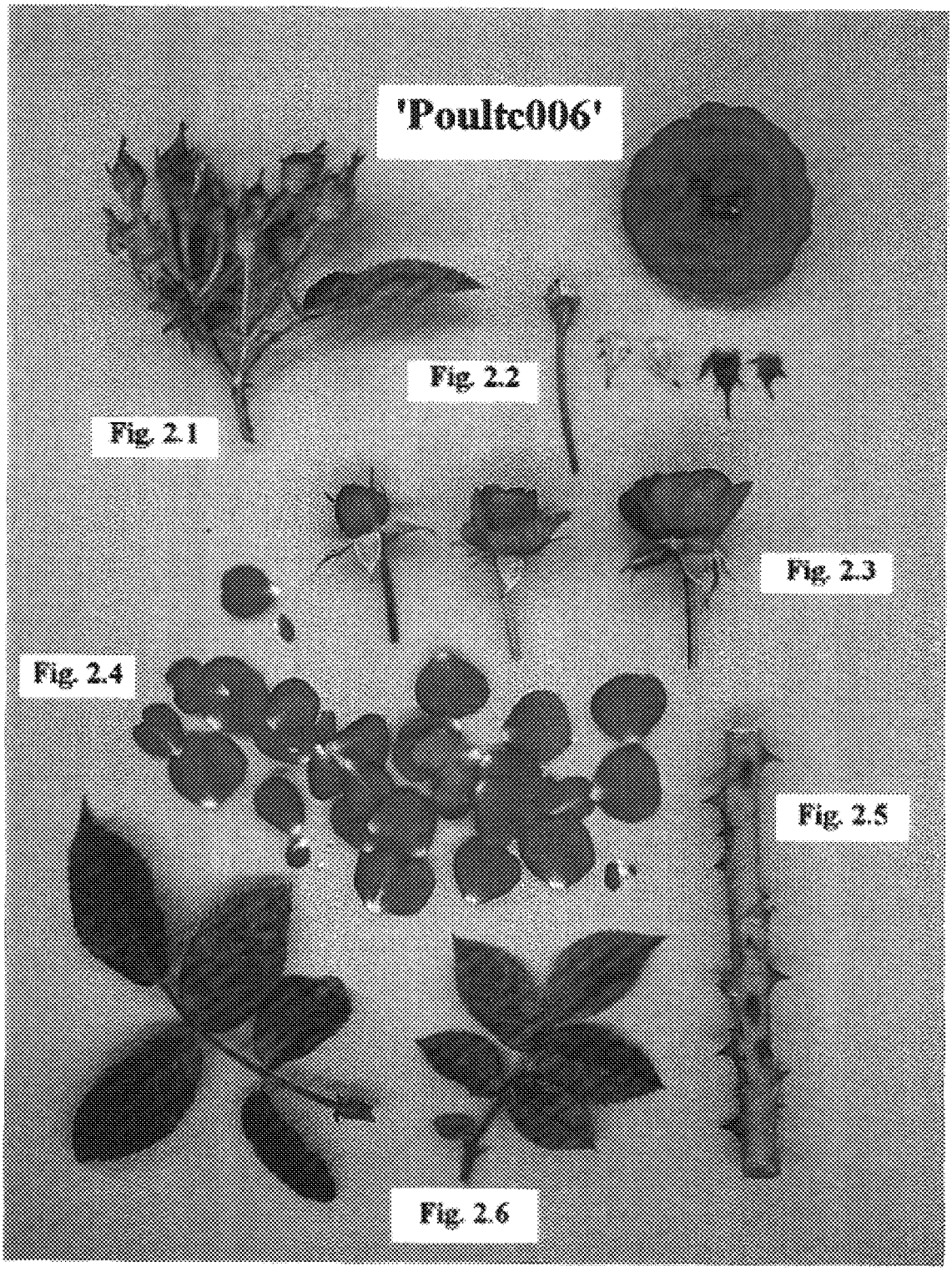
'Poultc006'
Fig. 2.1
Fig. 2.2
Fig. 2.3
Fig. 2.4
Fig. 2.5
Fig. 2.6

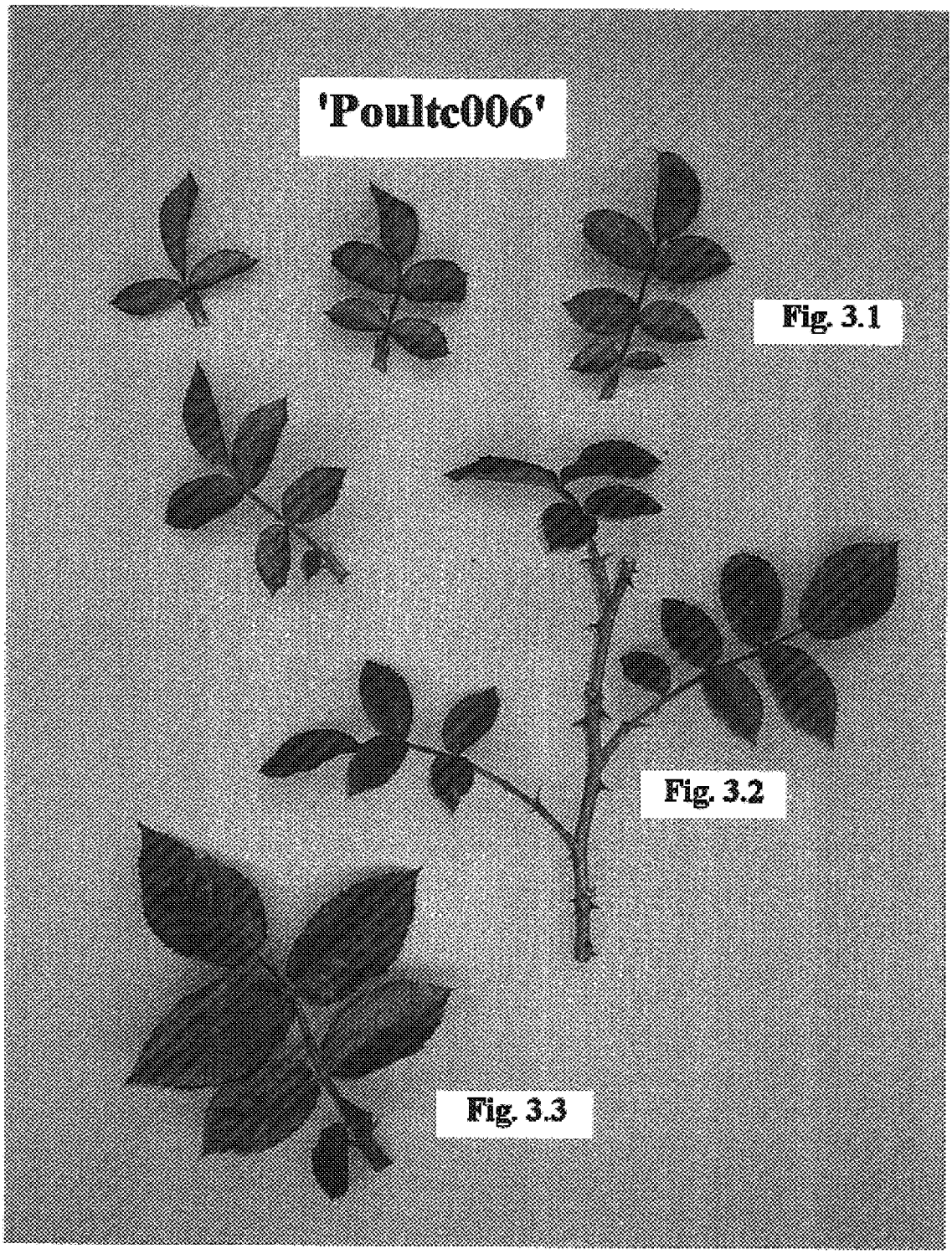
'Poultc006'
Fig. 3.1
Fig. 3.2
Fig. 3.3